United States Patent [19]

Green et al.

[11] 4,027,020

[45] May 31, 1977

[54] RANDOMLY TERMINATED CAPPED POLYMERS

[75] Inventors: Harold A. Green, Havertown, Pa.; John J. Merianos, Jersey City; Alfonso N. Petrocci, Glen Rock, both of N.J.

[73] Assignee: Millmaster Onyx Corporation, New York, N.Y.

[22] Filed: Sept. 4, 1975

[21] Appl. No.: 610,168

Related U.S. Application Data

[63] Continuation-in-part of Ser. No. 518,596, Oct. 29, 1974, Pat. No. 3,931,319.

[52] U.S. Cl. .................. 424/248.56; 260/240 E; 260/567.6 P; 424/244; 424/248.57; 424/267; 424/329; 526/11.1
[51] Int. Cl.² .................. A01N 9/00; A01N 9/22; C07C 85/00; C07C 87/30
[58] Field of Search .................. 260/567.6 P, 240; 424/267, 244, 329, 248.56, 248.57

[56] References Cited

UNITED STATES PATENTS

| | | | |
|---|---|---|---|
| 1,797,877 | 3/1931 | Moore | 260/567.6 P |
| 2,261,002 | 10/1941 | Ritter | 260/567.6 P |
| 2,375,853 | 5/1945 | Kirby et al. | 260/567.6 P |
| 2,388,614 | 11/1945 | Kirby et al. | 260/567.6 P |
| 2,525,777 | 10/1950 | de Bernneville | 260/567.6 P |
| 2,817,664 | 12/1957 | Cavallito et al. | 260/567.6 P |
| 2,933,529 | 4/1960 | Hwa | 260/567.6 P |
| 3,079,436 | 2/1963 | Hwa | 260/567.6 P |
| 3,825,511 | 7/1974 | Markhart et al. | 526/259 |

FOREIGN PATENTS OR APPLICATIONS

| | | | |
|---|---|---|---|
| 536,017 | 4/1941 | United Kingdom | 260/567.6 P |
| 750,346 | 6/1956 | United Kingdom | 260/567.6 P |

*Primary Examiner*—Albert T. Meyers
*Assistant Examiner*—D. W. Robinson
*Attorney, Agent, or Firm*—Arthur A. Jacobs

[57] ABSTRACT

Anti-microbial polymeric quaternary ammonium compounds having linear chains which terminate in quaternary ammonium moieties, such compounds being formed by polymerization which is carried out in such a manner that the linear chains thereof are terminated in random fashion, the reaction resulting in the formation of the compounds being a one-step reaction between 1,4-dihalo-2-butene and a mixture of a difunctional tertiary amine and a monofunctional tertiary amine wherein the molar quantity of the difunctional amine is greater than the molar quantity of the monofunctional amine.

6 Claims, No Drawings

RANDOMLY TERMINATED CAPPED POLYMERS

This application is a continuation-in-part of application Ser. No. 518,596, filed Oct. 29, 1974 now U.S. Pat. No. 3,931,319.

This invention relates to a new class of anti-microbial agents which are very effective against bacteria and algae and to a somewhat lesser extent, against fungi. More particularly, this invention relates to quaternary ammonium polymers in which the ammonium moieties are part of the linear polymeric chains, and not branches appended to the linear chain. Even more particularly, this invention relates to such quaternary ammonium polymers in which the linear chains terminate in quaternary ammonium moieties, thereby making further chain propagation impossible under the conditions of the experimental procedure by which the polymers and synthesized. Furthermore, polymerization is carried out in such a manner that the chain lengths, and therefore the molecular weights, of the polymers vary over a wide range because polymerization is halted and the chains are terminated in random fashion. Accordingly, the products of this invention are called "randomly terminated" quaternary ammonium polymers.

The products of this invention may be synthesized by causing 1,4-dihalo-2-butene to react in a one-step reaction with a mixture of a difunctional tertiary amine and a monofunctional tertiary amine. The molar quantity of the difunctional amine must be considerably greater than the molar quantity of the monofunctional amine in the mixture, the molar ratios of diamine to monoamine being from about 2 to 1, to about 30 to 1.

In the starting materials the number of terminal halogen moieties in the 1,4-dihalo-2-butene should be approximately equal to the total number of tertiary amino groups. Since the diamine and the dihalo compounds each have two reactive equivalents, but the monoamine has only one reactive equivalent, the proper ratios of starting materials can be achieved when the number of moles of 1,4-dihalo-2-butene is approximately equal to the sum of the number of moles of diamine and one-half the number of moles of monoamine.

The difunctional tertiary amine may be represented by the structural formula:

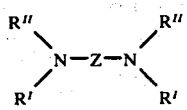

For purposes of clarification, Z represents either (1) a divalent aliphatic radical of from 2 to 10 carbon atoms containing from 0 to 2 hydroxyl substituents and from 0 to 2 ethylenic double bonds, and $R^I$ and $R^{II}$ may either be (A) the same or different and may be either (a) an alkyl group of from 1 to 20 carbon atoms having from 0 to 2 hydroxyl substituents, (b) benzyl, (c) benzyl in which the benzene moiety has one alkyl substituent of from 2 to 20 carbon atoms, and (d) benzyl in which the benzene moiety has from 1 to 5 methyl substituents; (B) $R^I$ and $R^{II}$, taken together with N, form a saturated or unsaturated heterocyclic ring of from 5 to 7 atoms; or (C) $R^I$ and $R^{II}$, taken together with N, may be combined with an oxygen atom to form a N-morpholino group; or (2) Z represents two divalent ethylene radicals, in which case $R^{II}$ is absent and $R^I$ represents (a) an aliphatic radical of from 1 to 20 carbon atoms having from 0 to 2 hydroxyl substituents, (b) benzyl, (c) benzyl in which the benzene moiety has an alkyl substituent of from 2 to 20 carbon atoms, or (d) benzyl in which the benzene moiety has from 1 to 5 methyl substituents; or (3) Z represents three divalent ethylene radicals in which case $R^I$ and $R^{II}$ are both absent.

The monotertiary amine may be represented by the structural formula:

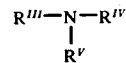

where (1) $R^{III}$ is an aliphatic radical of from 1 to 20 carbon atoms, having from 0 to 2 hydroxyl substituents, and $R^{IV}$ and $R^V$ may be either (a) the same or different and represent an aliphatic radical having from 1 to 4 carbon atoms with from 0 to 1 hydroxyl substituents; (b) taken together with N to form a saturated or unsaturated heterocyclic ring of from 5 to 7 atoms; (c) taken together with N, and combined with an oxygen atom to form a N-morpholino group; or where (2) $R^{III}$, $R^{IV}$, $R^V$ and N taken together, may represent quinoline, isoquinoline or hexamethylene tetramine.

In the parent application Ser. No. 518,596, mentioned above, a method was described wherein the polymeric quaternary compounds are made by a two-step synthesis. In the first step 1,4-dihalo-2-butene was reacted with slightly less than a molar quantity of a ditertiary amine. Under the conditions of this reaction, polymerization proceeds until the diamine is depleted. Because of the initial excess of dihalo butene over diamine in the reaction mixture, the polymeric chains have termini of halogen atoms, thereby making the ends of the chain reactive toward the addition of more amine. After the unreacted dichlorobutene is removed by extraction at the completion of the first step, a calculated quantity of monotertiary amine is added to the polymeric residue for the second step of the synthesis.

The chemical quaternization which ensues from the above reaction results in the formation of polymers with quaternary ammonium termini. Since these quaternized ends of the chain are incapable of further chain propagation reactions with dihalobutene, the polymer is said to be "capped" in the second step.

The second step mentioned above merely "caps" the polymeric products of the first step. Therefore, the chain lengths and molecular weights of the product are determined in the first step. Since the polymerization of the first step proceeds in a sustained fashion until all of the diamine is exhausted, the chain lengths are comparatively long because the number of condensations is comparatively high. Furthermore, since the propagation of chains was permitted to proceed uninterruptedly under conditions where each chain has equal probability to participate in the propagation reaction, the product of the first step, and subsequently the product of the second step, is a mixture of polymeric products whose chain lengths and molecular weights fall within a comparatively narrow range.

In accordance with the present invention on the other hand, the products are made by a single-step synthesis in which both ditertiary amine and monotertiary amine are mixed simultaneously with the 1,4-dihalo-2-butene, there being about a 1:1 ratio of halogen equivalents to the total number of tertiary amine equivalents. The molar ratio of diamine to monoamine in the initial reaction mixture is about 2:1 to about 30:1. The reaction takes place at reflux temperature, which is usually between about 50°–70° C, while the reaction time may vary depending on the reactants as well as the temperature, but is usually about 1 to 10 hours.

In both the present invention and that described in the parent application, the terminal halogen atoms of a chain may participate in chain propagation reactions by being displaced by one of the amine groups of a diamine, thereby making a quaternary nitrogen. Chain propagation is possible because the second amine of the diamine is capable of reacting with a dihalo molecule. However, in the present invention, there is also an alternative route. The terminal halogen of a chain may react with a monoamine, instead of a diamine. The reaction with a monoamine gives rise to a quaternary ammonium terminus which is incapable of further chain propagation by reaction with a dihalo molecule. In this manner, any chain may become "capped" while other chains are propagating. Therefore, the product of the present invention, in which both diamine and monoamine are used in the initial reaction mixture, is the resultant of two competing reactions, one a propagation reaction when the diamine reacts with the terminal halogen and the other a "capping" reaction, when the monoamine reacts.

The products made by the two different processes are unlike both in their chemical and physical properties. In this respect, because of the presence of monoamine during chain propagation there is always a possibility that a chain termination reaction will occur and terminate chain propagation abruptly. Therefore, every chain cannot grow uninterruptedly. Some chains will continue to grow while others will terminate, depending on whether the terminal halogen reacts with a diamine or monoamine.

Furthermore, some chains are terminated quite early, leaving only small chains, whereas other chains are terminated only after having undergone a large number of propagation reactions. Termination occurs in a statistically random fashion. Therefore, the chain lengths vary from very short to very long, and the molecular weights vary from low to high, over a comparatively wide range.

This is in contrast to the prior products in which the polymeric quaternary compounds were all of comparatively high molecular weights, and varied over a comparatively narrow range.

The following examples exemplify the present invention:

EXAMPLE 1

522 grams of morpholine (6 moles) were cooled to 20° C and 125 grams of 1,4-dichloro-2-butene (1 mole) were added dropwise with constant stirring and cooling to keep the temperature at 50°–60° C. The entire addition took about 1 hour, and stirring was continued for about one more hour. While stirring, 150 grams of water was poured into the reaction mixture, followed by 200 grams of 50% sodium hydroxide solution, then the mixture was allowed to separate.

The organic layer was removed, and the unreacted morpholine was removed by distillation under reduced pressure. The residue was washed with water and filtered, yielding a yellow solid melting at 79°–83° C. This was 1,4-bis-(N-morpholino)-2-butene.

Since the purpose of the excess morpholine was to act as an acid acceptor, the experiment was repeated, but with 212 grams of sodium carbonate (2 moles) replacing the excess 174 grams of morpholine (4 moles). The yield of 1,4-bis-(N-morpholino)-2-butene was about the same as the previous synthesis.

This reaction was repeated using 0.1 mole of 1,4-dichloro-2-butene and 0.6 mole of the following amines in place of morpholine: piperidine, homopiperidine, diethanolamine, dimethylamine, dipropylamine, dibutylamine, di-(2-ethylhexyl) amine, dioctylamine, didecylamine, didodecylamine, N-methyl propylamine, N-methyl butylamine, N-methyl hexylamine, N-methyl octylamine, N-methyl decylamine, N-methyl dodecylamine. All of these 1,4-bis-amino-2-butenes were liquids, and were recovered from their aqueous mixtures by partitioning.

EXAMPLE 2

28.4 grams of 1,4-bis-dimethylamino-2-butene (0.2 moles) and 1.49 grams of triethanolamine (0.01 moles) were dissolved in about 55.5 grams of water in a round-bottom flask fitted with a stirrer and reflux condenser, and 25.63 grams of 1,4-dichloro-2-butene (0.205 moles) were added slowly while the mixture was stirred. The reaction mixture was heated to 60°–70° C and maintained at that temperature, with stirring, for about 6 hours. The reaction was 98% complete, as indicated by ionic chloride analysis. The residue contained about 50%, by weight, of active material.

The procedure of Example 2 was repeated several times using different proportions of reactants, as follows:

|  | Example 3 | Example 4 | Example 5 | Example 6 | Example 7 |
| --- | --- | --- | --- | --- | --- |
| 1,4-bis-dimethylamino-2-butene | 28.4 grams (0.2 moles) | 28.4 grams (0.2 moles) | 28.4 grams (0.2 moles) | 28.4 grams (0.2 moles) | 28.4 grams (0.2 moles) |
| triethanol amine | 2.98 grams (0.02 moles) | 5.96 grams (0.04 moles) | 8.94 grams (0.06 moles) | 11.92 grams (0.08 moles) | 14.9 grams (0.1 moles) |
| 1,4-dichloro-2-butene | 26.25 grams (0.21 moles) | 27.5 grams (0.22 moles) | 28.3 grams (0.23 moles) | 30.0 grams (0.24 mols) | 31.3 grams (0.25 moles) |
| Water | 57.7 grams | 61.9 grams | 65.7 grams | 70.3 grams | 74.6 grams |

The procedure of Example 2 was again repeated, except that the following reactants were used:

EXAMPLE 8

28.4 grams of 1,4-bis-dimethylamino-2-butene (0.2 moles)
1.94 grams of N-methyl morpholine (0.02 moles)
26.25 grams of 1,4-dichloro-2-butene (0.21 moles)
56.6 grams of water

EXAMPLE 9

28.4 grams of 1,4-bis-dimethylamino-2-butene (0.2 moles)
2.00 grams of N-methyl piperidine (0.02 moles)
26.25 grams of 1,4-dichloro-2-butene (0.21 moles)
56.7 grams of water

EXAMPLE 10

28.4 grams of 1,4-bis-dimethylamino-2-butene (0.2 moles)
2.06 grams of N-methyl homopiperidine (0.02 moles)
26.5 grams of 1,4-dichloro-2-butene (0.21 moles)
56.7 grams of water

EXAMPLE 11

28.4 grams of 1,4-bis-dimethylamino-2-butene (0.2 moles)
1.7 grams of N-methyl pyrrolidine (0.02 moles)
26.5 grams of 1,4-dichloro-2-butene (0.21 moles)
56.6 grams of water

EXAMPLE 12

28.4 grams of 1,4-bis-dimethylamino-2-butene (0.2 moles)
2.02 grams of butyldimethylamine (0.02 moles)
26.5 grams of 1,4-dichloro-2-butene (0.21 moles)
56.9 grams of water

EXAMPLE 13

28.4 grams of 1,4-bis-dimethylamino-2-butene (0.2 moles)
2.3 grams of pentyldimethylamine (0.02 moles)
26.5 grams of 1,4-dichloro-2-butene (0.21 moles)
57.2 grams of water

EXAMPLE 14

28.4 grams of 1,4-bis-dimethylamino-2-butene (0.2 moles)
2.58 grams of hexyldimethylamine (0.02 moles)
26.5 grams of 1,4-dichloro-2-butene (0.21 moles)
57.5 grams of water

EXAMPLE 15

28.4 grams of 1,4-bis-dimethylamino-2-butene (0.2 moles)
2.86 grams of heptyldimethylamine (0.02 moles)
26.5 grams of 1,4-dichloro-2-butene (0.21 moles)
57.8 grams of water

EXAMPLE 16

28.4 grams of 1,4-bis-dimethylamino-2-butene (0.2 moles)
3.14 grams of octyldimethylamine (0.02 moles)
26.5 grams of 1,4-dichloro-2-butene (0.21 moles)
58.1 grams of water

EXAMPLE 17

28.4 grams of 1,4-bis-dimethylamino-2-butene (0.2 moles)
3.42 grams of nonyldimethylamine (0.02 moles)
26.5 grams of 1,4-dichloro-2-butene (0.21 moles)
58.3 grams of water

EXAMPLE 18

28.4 grams of 1,4-bis-dimethylamino-2-butene (0.2 moles)
3.7 grams of decyldimethylamine (0.02 moles)
26.5 grams of 1,4-dichloro-2-butene (0.21 moles)
58.6 grams of water

EXAMPLE 19

28.4 grams of 1,4-bis-dimethylamino-2-butene (0.2 moles)
3.98 grams of undecyldimethylamine (0.02 moles)
26.5 grams of 1,4-dichloro-2-butene (0.21 moles)
58.9 grams of water

EXAMPLE 20

28.4 grams of 1,4-bis-dimethylamino-2-butene (0.2 moles)
4.26 grams of dodecyldimethylamine (0.02 moles)
26.5 grams of 1,4-dichloro-2-butene (0.21 moles)
59.2 grams of water

EXAMPLE 21

28.4 grams of 1,4-bis-dimethylamino-2-butene (0.2 moles)
2.7 grams of benzyldimethylamine (0.02 moles)
26.5 grams of 1,4-dichloro-2-butene (0.21 moles)
57.6 grams of water

EXAMPLE 22

28.4 grams of 1,4-bis-dimethylamino-2-butene (0.2 moles)
2.62 grams of quinoline (0.02 moles)
26.5 grams of 1,4-dichloro-2-butene (0.21 moles)
57.5 grams of water.

EXAMPLE 23

28.4 grams of 1,4-bis-dimethylamino-2-butene (0.2 moles)
2.62 grams of isoquinoline (0.02 moles)
26.5 grams of 1,4-dichloro-2-butene (0.21 moles)
57.5 grams of water

EXAMPLE 24

28.4 grams of 1,4-bis-dimethylamino-2-butene (0.2 moles)
2.8 grams of hexamethylenetetramine (0.02 moles)
26.5 grams of 1,4-dichloro-2-butene (0.21 moles)
57.7 grams of water Although in Examples 2 to 24 above, the difunctional tertiary amine 1,4-bis-dimethylamino-2-butene was utilized, any of the other difunctional tertiary amines, as disclosed in Example 1, may be substituted in equivalent molar amounts. Illustrative of such other difunctional amines are, for example, 1,4-bis-(N-morpholino)-2-butene; 1,4-N,N'-dimethylpiperazine; 1,4-diazabicyclo (2.2.2) octane; N,N,N',N'-tetramethylethylene diamine; N,N,N',N'-tetra-(2-hydroxylpropyl)-ethylene diamine; 1,3-bis-(dimethylamino)-2-hydroxypropane; and 1,4-di-(N-homopiperidino)-2-butene.

Furthermore, although only 1,4-dichloro-2-butene has been illustrated above, 1,4-dibromo or 1,4-diiodo-2-butene may be substituted.

EXAMPLE 25

28.4 grams of 1,4-bis-dimethylamino-2-butene (0.2 moles)
1.01 grams of butyldimethylamine (0.01 moles)
25.63 grams of 1,4-dichloro-2-butene (0.205 moles)
55.04 grams of water

EXAMPLE 26

28.4 grams of 1,4-bis-dimethylamino-2-butene (0.2 moles)
0.97 grams of N-methyl morpholine (0.01 moles)
25.63 grams of 1,4-dichloro-2-butene (0.205 moles)
55.0 grams of water

EXAMPLE 27

The "Broth Dilution Test" method was used to assay the antimicrobial properties of the products. In this method, 1.0 ml. of a solution of the material being tested was added to 9.0 ml. of a suitable broth culture medium in a test tube. A series of such test tubes was prepared so that there was presented a stepwise decrease in the concentrations being tested, from 0.1% (1000 ppm) to 0.005% (50 ppm). Each tube was then inoculated with 0.1 ml. of either a 24-hour broth culture of test bacteria, or a 14-day aqueous spore suspension of test fungi. The testing program was designed so that every concentration of every material was inoculated separately by each organism used in the test.

The test organisms employed were:

*Escherchia coli* (E.c.)
*Pseudomonas aeruginosa* (Ps.a.)
*Staphylococcus aureus* (S.a.)
*Streptococcus faecalis* (S.f.)
*Aspergillus niger* (A.n.)
*Penicilium expansum* (P.e.)

After inoculation, the tubes were incubated as follows:

72 hours at 37° C for bacteria
14 days at 28° C for fungi

Following incubation, the tubes were examined for the presence or absence of macroscopic growth as evidenced by the presence or absence of turbidity.

The lowest concentration of the material being tested at which macroscopic growth was not evident was designated as the "Minimum Inhibitory Level" (M.I.L.).

Table 1, following shows the M.I.L. of the products that were tested. The inhibitory concentrations are shown in parts per million:

Table 1

| Synthesized Product in Example No. | Gram Positive | | Gram Negative | | Fungi | |
|---|---|---|---|---|---|---|
| | E.c. | Ps.a. | S.a. | S.f. | A.n. | P.e. |
| 1 | 1000 | 1000 | 1000 | 1000 | >1000 | >1000 |
| 2 | 50 | 50 | 50 | 50 | >1000 | >1000 |
| 7 | 50 | 50 | 50 | 50 | >1000 | >1000 |
| 24 | 1000 | 1000 | 1000 | 1000 | >1000 | >1000 |
| 11 | 50 | 50 | 50 | 50 | >1000 | >1000 |
| 23 | 100 | 500 | 100 | 100 | >1000 | >1000 |
| 15 | 1000 | 1000 | 1000 | 1000 | >1000 | >1000 |
| 17 | 1000 | 1000 | 1000 | 1000 | >1000 | >1000 |

The results of these tests show that every compound tested has anti-bacterial properties in concentrations as low as 0.1%, and even lower in many cases.

EXAMPLE 28

In order to estimate the bactericidal power of these compounds, the product prepared in Example 3 was assayed using the "Water Treatment Test".

The product was dissolved in sterile distilled water and diluted to the test concentration. Then 50 ml. of test solution was added aseptically to previously sterilized cotton-stoppered 125 ml. Erlenmeyer flasks. One set of flasks containing the product at concentrations of 25 ppm., 50 ppm., 100 ppm., 150 ppm., 200 ppm., 250 ppm., and 300 ppm, was inoculated by introducing into each flask 0.5 ml. of a 1/10 nutrient broth dilution of a 24-hour nutrient broth culture of Aerobacter aerogenes. Another set of flasks containing the product at the same concentrations was inoculated by introducing into each flask 0.5 ml of a 1/10 nutrient broth dilution of a 24-hour nutrient broth culture of Pseudomonas aeruginosa.

At intervals of 30, 60 and 180 minutes following inoculation a 1.0 ml. aliquot was withdrawn from each flask and added to 9.0 ml. of sterile azolectin/"Tween 80" neutralizer from which additional tenfold serial dilutions were prepared in sterile neutralizer solution.

Nutrient agar plates were prepared from $1 \times 10^{-2}$ and $1 \times 10^{-3}$ dilutions.

Simultaneously with each set of flasks, a control of sterile distilled water was similarly inoculated and aliquots were taken at the same time intervals at $1 \times 10^{-4}$, $1 \times 10^{-5}$, and $1 \times 10^{-6}$ dilutions.

For additional control purposes, and also for comparison purposes, simultaneous assays were performed with each set of flasks on "BTC 776", a powerful bactericidal agent used in water treatment, the chemical name of which is alkyl benzyl dimethyl ammonium chloride. It is manufactured and sold By Onyx Chemical Co. of Jersey City, N.J.

Table 2 shows the number of survivors of Aerobacter aerogenes and Table 3 shows the number of survivors of Pseudomonas aeruginosa ATCC #15442, following exposure at different concentrations for the indicated periods of time. The numbers in the table must be multiplied by $1 \times 10^2$. Concentrations of the materials being tested are given in parts per million.

Table 2

| Compound (Example No.) | Concentration (ppm) | Aerobacter Aerogenes No. of Surviving Bacteria per ml. ($\times 10^2$) After | | |
|---|---|---|---|---|
| | | 30 Min. | 60 Min. | 180 Min. |
| 3 | 5 | 78 | 43 | 3 |
| | 5 | 89 | 45 | 1 |
| | 5 | 39 | 19 | 0 |
| | 5 | 59 | 15 | 0 |
| | 5 | 47 | 12 | 0 |
| | 5 | 37 | 14 | 0 |
| | 5 | 57 | 7 | 0 |
| | 10 | 23 | 1.5 | 0 |
| | 10 | 27 | 3 | 0 |
| | 10 | 22 | 4 | 0 |
| | 10 | 20 | 2 | 0 |
| | 10 | 21 | 3 | 0 |
| | 10 | 21 | 3 | 0 |
| | 10 | 16 | 3 | 0 |
| | 15 | 0 | 0 | 0 |
| | 25 | 0 | 0 | 0 |
| | 25 | 0 | 0 | 0 |
| | 0 | 20,900 | 26,500 | 28,700 |
| BTC (Control) | 10 | 49 | 10 | 0 |
| | 10 | 37 | 8 | 0 |
| | 10 | 32 | 10 | 0 |
| | 10 | 43 | 14 | 0 |
| | 20 | 1 | 0 | 0 |
| | 20 | 2 | 0 | 0 |
| | 20 | 6 | 0 | 0 |
| | 20 | 4 | 0 | 0 |

Table 3

| Compound (Example No.) | Concentration (ppm) | Pseudomonas Aeruginosa No. of Surviving Bacteria per ml. ($\times 10^2$) After | | |
|---|---|---|---|---|
| | | 30 Min. | 60 Min. | 180 Min. |
| 3 | 20 | 9 | 0 | 0 |
| | 20 | 15 | 1 | 0 |
| | 20 | 13 | 0 | 0 |
| | 25 | 1 | 0 | 0 |
| | 25 | 0 | 0 | 0 |
| | 0 | 92,500 | 91,500 | 91,000 |
| BTC (Control) | 10 | 1,260 | 180 | 0 |
| | 10 | 1,380 | 123 | 0 |
| | 10 | 1,460 | 118 | 0 |
| | 10 | 1,500 | 192 | 0 |

Table 3-continued

| Compound (Example No.) | Concentration (ppm) | Pseudomonas Aeruginosa No. of Surviving Bacteria per ml. ($\times 10^2$) After | | |
|---|---|---|---|---|
| | | 30 Min. | 60 Min. | 180 Min. |
| BTC (Control) | 15 | 214 | 16 | 0 |
| | 15 | 235 | 18 | 0 |
| | 20 | 208 | 57 | 0 |
| | 20 | 137 | 15 | 0 |
| | 20 | 145 | 18 | 0 |
| | 20 | 162 | 17 | 0 |

The compounds of this invention are all very soluble in water and insoluble in organic solvents such as isopropanol, acetone, hexane, trichloroethane, toluene, and the like. They are, furthermore, non-foaming, shich is an important property because it makes these compounds suitable for use as anti-microbial agents in products and processes where the generation of foam would be undesirable.

The invention claimed is:

1. A product formed by a one-step reaction between 1,4-dihalo-2-butene and a mixture of a difunctional tertiary amine with a monofunctional tertiary amine, the molar ratio of the difunctional amine to the monofunctional amine being from about 2:1 to 30:1, the number of moles of the 1,4-dihalo-2-butene being about equal to the sum of the number of moles of the difunctional tertiary amine plus one-half the number of moles of the monofunctional amine, the reaction being effected at a temperature of between about 50°–70° C and during a time interval of between about 1 to 10 hours, the difunctional tertiary amime having the formula:

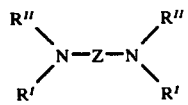

wherein Z represents either (1) a divalent aliphatic radical of from 2 to 10 carbon atoms containing from 0 to 2 hydroxyl substituents and from 0 to 2 ethylenic double bonds, and $R^I$ and $R^{II}$ may either be (A) the same or different and may be either (a) an alkyl group of from 1 to 20 carbon atoms having from 0 to 2 hydroxyl substituents, (b) benzyl, (c) benzyl in which the benzene moiety has one alkyl substituent of from 2 to 20 carbon atoms, or (d) benzyl in which the benzene moiety has from 1 to 5 methyl substituents; (B) $R^I$ and $R^{II}$, taken together with N, form a saturated or unsaturated heterocyclic ring of from 5 to 7 atoms; or (C) $R^I$ and $R^{II}$, taken together with N, and combined with an oxygen atom, form a N-morpholino group; or (2) Z represents two divalent ethylene radicals, in which case $R^{II}$ is absent and $R^I$ represents (a) an aliphatic radical of from 1 to 20 carbon atoms having from 0 to 2 hydroxyl substituents, (b) benzyl, (c) benzyl in which the benzene moiety has an alkyl substituent of from 2 to 20 carbon atoms; or (d) benzyl in which the benzene moiety has from 1 to 5 methyl substituents; or (3) Z represents three divalent ethylene radicals in which case $R^I$ and $R^{II}$ are both absent; and the monotertiary amine having the formula:

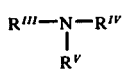

where (1) $R^{III}$ is an aliphatic radical of from 1 to 20 carbon atoms, having from 0 to 2 hydroxyl substituents, and $R^{IV}$ and $R^V$ may either be (a) the same or different and represent an aliphatic radical having from 1 to 4 carbon atoms with from 0 to 1 hydroxyl substituents, (b) taken together with N to form a saturated or unsaturated heterocyclic ring of from 5 to 7 atoms; (c) taken together with N, and combined with an oxygen atom to form a N-morpholino group; or where (2) $R^{III}$, $R^{IV}$, $R^V$ and N, taken together, represent quinoline, isoquinoline or hexamethylene tetramine.

2. The product of claim 1 wherein the difunctional tertiary amine is selected from the group consisting of 1,4-bis-(N-morpholino)-2-butene; 1,4-bis-dimethylamino-2-butene; 1,4-N,N'-dimethylpiperazine; 1,4-diazabicyclo (2.2.2) octane; N,N,N',N'-tetramethylethylene diamine; N,N,N',N'-tetra-(2-hydroxypropyl)-ethylene diamine; 1,3-bis-(dimethylamino)-2-hydroxypropane; and 1,4-di-(N-homopiperidino)-2-butene.

3. The product of claim 1 wherein the monofunctional tertiary amine is selected from the group consisting of triethanolamine; N-methyl morpholine; N-methyl piperidine; N-methyl homopiperidine; N-methyl pyrrolidine; butyl-dimethylamine; pentyldimethylamine; hexyldimethylamine; heptyldimethylamine; octyldimethylamine; nonyldimethylamine; decyldimethylamine; undecyldimethylamine; dodecyldimethylamine; hexamethylene tetramine; benzyldimethylamine; quinoline; and isoquinoline.

4. A method of controlling the proliferation of deleterious microorganisms which comprises applying to said microorganisms an amount sufficient to inhibit their proliferation of a product formed by a one-step reaction between 1,4-di-halo-2-butene and a mixture of a difunctional tertiary amine with a monofunctional tertiary amine, the molar ratio of the difunctional amine to the monofunctional amine being from about 2:1 to about 30:1, the number of moles of the 1,4-di-halo-2-butene being about equal to the sum of the number of moles of the difunctional tertiary amine plus one-half the number of moles of the monofunctional amine, the reaction being effected at a temperature of between about 50°–70° C and during a time interval of between about 1 to 10 hours; the difunctional tertiary amine having the formula:

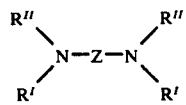

wherein Z represents either (1) a divalent aliphatic radical of from 2 to 10 carbon atoms containing from 0 to 2 hydroxyl substituents and from 0 to 2 ethylenic double bonds, and $R^I$ and $R^{II}$ may either be (A) the same or different and may be either (a) an alkyl group of from 1 to 20 carbon atoms having from 0 to 2 hydroxyl substituents, (b) benzyl, (c) benzyl in which the benzene moiety has one alkyl substituent of from 2 to 20 carbon atoms or (d) benzyl in which the benzene moiety has from 1 to 5 methyl substituents; (B) $R^I$ and $R^{II}$, taken together with N, form a saturated or unsaturated heterocyclic ring of from 5 to 7 atoms; or (C) $R^I$ and $R^{II}$, taken together with N, and combined with an oxygen atom, form a N-morpholino group; or (2) Z represents two divalent ethylene radicals, in which case $R^{II}$ is absent and $R^{I}$ represents (a) an aliphatic radical of from 1 to 20 carbon atoms having from 0 to 2 hydroxyl substituents, (b) benzyl, (c) benzyl in which the benzene moiety has an alkyl substituent of from 2 to 20 carbon atoms; or (d) benzyl in which the benzene moiety has from 1 to 5 methyl substituents; or (3) Z represents three divalent ethylene radicals in which case $R^{I}$ and $R^{II}$ are both absent; the monotertiary amine having the formula:

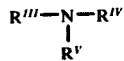

where (1) $R^{III}$ is an aliphatic radical of from 1 to 20 carbon atoms, having from 0 to 2 hydroxyl substituents, and $R^{IV}$ and $R^{V}$ may be either (a) the same or different and represent an aliphatic radical having from 1 to 4 carbon atoms with from 0 to 1 hydroxyl substituents; (b) taken together with N to form a saturated or unsaturated heterocyclic ring of from 5 to 7 atoms; (c) taken together with N, and combined with an oxygen atom to form a N-morpholino group; or where (2) $R^{III}$, $R^{IV}$, $R^{V}$ and N, taken together, represent quinoline, isoquinoline or hexamethylene tetramine.

5. The method of claim 4 wherein the difunctional tertiary amine is selected from the group consisting of 1,4-bis-(N-morpholino)-2-butene; 1,4-bis-dimethylamino-2-butene; 1,4-N,N'-dimethylpiperazine; 1,4-diazabicyclo (2.2.2) octane; N,N,N',N'-tetramethylethylene diamine; N,N,N',N'-tetra-(2-hydroxypropyl)-ethylene diamine; 1,3-bis-(dimethylamino)-2-hydroxypropane; and 1,4-di-(N-homopiperidino)-2-butene.

6. The method of claim 4 wherein the monofunctional tertiary amine is selected from the group consisting of triethanolamine; N-methyl morpholine; N-methyl piperidine; N-methyl homopiperidine; N-methyl pyrrolidine; butyl-dimethylamine; pentyldimethylamine; hexyldimethylamine; heptyldimethylamine; octyldimethylamine; nonyldimethylamine; decyldimethylamine; undecyldimethylamine; dodecyldimethylamine; hexamethylene tetramine; benzyldimethylamine; quinoline; and isoquinoline.

* * * * *